(12) United States Patent
Yodfat et al.

(10) Patent No.: US 8,734,383 B2
(45) Date of Patent: May 27, 2014

(54) METHOD AND DEVICE FOR IMPROVING GLYCEMIC CONTROL BASED ON RESIDUAL INSULIN

(75) Inventors: Ofer Yodfat, Modi'in (IL); Iddo Gescheit, Tel-Aviv (IL); Gali Shapira, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 13 days.

(21) Appl. No.: 13/380,287

(22) PCT Filed: Jun. 23, 2010

(86) PCT No.: PCT/IL2010/000501
§ 371 (c)(1),
(2), (4) Date: May 16, 2012

(87) PCT Pub. No.: WO2010/150257
PCT Pub. Date: Dec. 29, 2010

(65) Prior Publication Data
US 2012/0220939 A1 Aug. 30, 2012

Related U.S. Application Data

(60) Provisional application No. 61/220,204, filed on Jun. 25, 2009.

(51) Int. Cl.
*A61M 5/168* (2006.01)
*A61M 5/172* (2006.01)
*A61B 5/145* (2006.01)
*A61B 5/00* (2006.01)

(52) U.S. Cl.
CPC ............. *A61M 5/168* (2013.01); *A61M 5/1723* (2013.01); *A61B 5/14532* (2013.01); *A61B 5/4839* (2013.01)
USPC ............................................ 604/66; 604/151

(58) Field of Classification Search
USPC .......................................... 604/66, 151; 705/2
See application file for complete search history.

(56) References Cited

U.S. PATENT DOCUMENTS 6,936,029 B2 8/2005 Mann et al.
2007/0106218 A1 5/2007 Yodfat et al.
(Continued)

FOREIGN PATENT DOCUMENTS

WO WO 2008/078319 A1 7/2008
WO WO 2009/060433 A1 5/2009
(Continued)

OTHER PUBLICATIONS

DCCT Trial, N. Engl J. Med 1993; 329: 977-986.
(Continued)

*Primary Examiner* — Quynh-Nhu H Vu
(74) *Attorney, Agent, or Firm* — Roche Diagnostics Operations, Inc.

(57) ABSTRACT

Disclosed are systems, devices, and methods, including a system that includes a processor-based device implementing at least a residual insulin (RI) determination unit configured to determine a residual insulin in the patient's body at a particular time instance based on bolus doses previously delivered to the body of the patient, each bolus dose being associated with at least one dose value and a time representative of the time that dose value was delivered to the patient's body, and based on dose dependent RI time records that each includes at least a dose value and an associated duration value representative of dose-dependent duration of therapeutic effectiveness of the associated at least the dose value. The system also includes a pump to controllably dispense the insulin from a reservoir to the body of the patient based on the residual insulin determined by the RI determination unit.

20 Claims, 7 Drawing Sheets

(56) References Cited

U.S. PATENT DOCUMENTS

| | | | |
|---|---|---|---|
| 2007/0191702 A1 | 8/2007 | Yodfat et al. | |
| 2008/0172031 A1 | 7/2008 | Blomquist | |
| 2008/0234663 A1* | 9/2008 | Yodfat et al. | 604/890.1 |
| 2010/0017141 A1 | 1/2010 | Campbell et al. | |
| 2011/0106050 A1* | 5/2011 | Yodfat et al. | 604/504 |

FOREIGN PATENT DOCUMENTS

| | | |
|---|---|---|
| WO | WO 2009/066288 A1 | 5/2009 |
| WO | WO 2009/125398 A2 | 10/2009 |
| WO | WO 2009/133558 A2 | 11/2009 |

OTHER PUBLICATIONS

UKPDS Trial, Lancet 1998; 352: 837-853.
BMJ 1998; 317, (7160): 703-13.
EDIC Trial, N Engl J Med 2005; 353, (25): 2643-53.
Journal of Diabetes Science and Technology, 2007 vol. I (5), 780-793.
International Search Report for PCT Application No. PCT/IL2010/000501 date Mar. 10, 2011.

* cited by examiner

| Dose Given [IU] | Units left to work after: | | | | |
|---|---|---|---|---|---|
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

METHOD AND DEVICE FOR IMPROVING GLYCEMIC CONTROL BASED ON RESIDUAL INSULIN

CROSS-REFERENCE TO RELATED APPLICATION

The present application is a 35 U.S.C. §371 national stage entry of PCT/IL2010/000501, which has an international filing date of Jun. 23, 2010, and claims benefit and priority to U.S. Provisional Patent Application No. 61/220,204, filed on Jun. 25, 2009, entitled "A Method and Device for Improving Glycemic Control by Adjusting Remaining Insulin to Dose", the contents of which are hereby incorporated by reference in their entireties.

FIELD

A method, a system and a device for sustained medical infusion of therapeutic fluids to patients are described. Some embodiments relate to portable infusion systems and/or devices, and to a method for infusion that includes administering a therapeutic fluid according to patient's parameters. Some embodiments relate to an insulin-dispensing system and/or device configured to sense glucose levels of a patient and to a method for infusing insulin after adjusting the duration of insulin action according to the dose of administered insulin.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and, secrete insulin according to the blood glucose levels, maintaining near constant glucose levels in the body.

Much of the burden of the disease to the user and to health care resources is due to the long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery accordingly can be of utmost importance.

Insulin pumps have been available which deliver rapid acting insulin (e.g. Lispro, Aspart, etc.) 24 hours a day through a catheter placed under the skin. Rapid acting insulin effect begins in about 10 minutes, peaks at one to one and a half hours and ends in about two to six hours after the administration. The interval between insulin injection and end of its activity is defined as Duration of Insulin Activity (DIA) or Residual/Remaining Insulin time (RI time).

Figure 1:
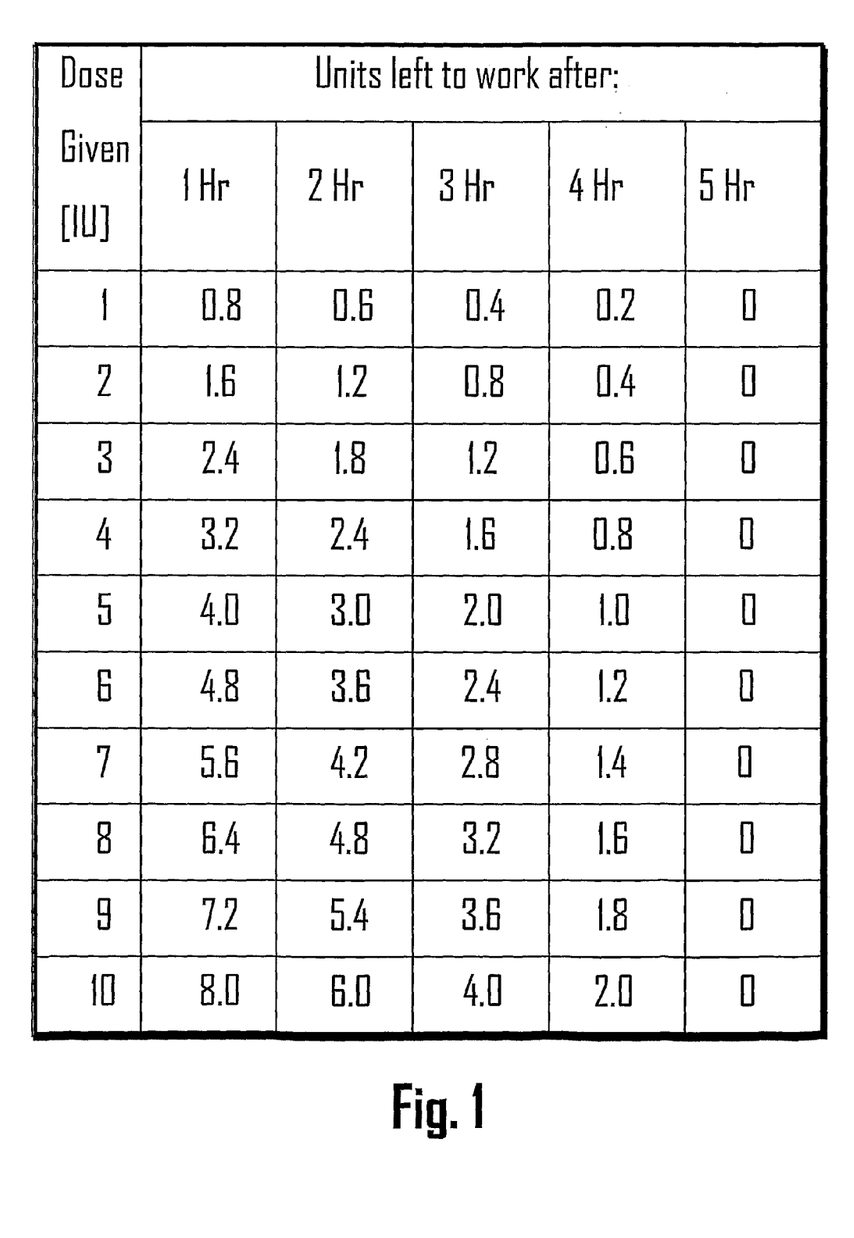
FIG. 1 is a chart of residual insulin of RI time of 5 hours after insulin Lispro bolus administration (dose independent RI time).

A simple rule can be applied to calculate the duration of insulin activity, i.e., the DIA. It is often stated that each hour after bolus dose administration, 20% of the dose becomes effective, so that after 5 hours there is no active insulin remaining in the body. FIG. 1 shows the insulin consumption according to the described rule (adapted from Using Insulin© 2003). One of the major advantages of using insulin pumps is the convenience of insulin bolus administration at any desired time. However, boluses may overlap and it can be useful to know the amount of active insulin that is still "working"/effective in the body, i.e. the RI. Accumulation of insulin may lead to life-threatening hypoglycemia. This is especially important at bedtime since users are usually unaware of nocturnal hypoglycemia.

Conventional insulin pumps can apply the abovementioned rule to calculate the residual insulin and subtract the calculated value from administered bolus. For example, based on FIG. 1, if a desired 5 U bolus is administered 2 hours after a 6 U bolus, the RI=3.6 U and the actually delivered bolus should be 1.4 U (5 U-3.6 U). If however an additional bolus of 5 U was delivered 4 hours before the desired 5 U bolus administration, the total RI is 3.6 (6 U minus 40% of 6 U) plus 1 U (5 U minus 80% of 5 U). The total RI (i.e. 3.6 U+1 U=4.6 U) is then subtracted from the desired 5 U bolus to yield a bolus dose of merely 0.4 U (5 U-4.6 U).

Bolus recommendations provided by portable insulin pumps that include bolus calculators (and other types of bolus determining units) take into consideration the residual insulin. For example, in U.S. Pat. No. 6,936,029 assigned to Medtronic Minimed, a pump provided with a bolus calculator and an algorithm for calculating the amount of insulin to be administered is described. The algorithm is based on a formula for calculating a bolus, depending on the user's insulin sensitivity (IS), carbohydrate-to-insulin ration (CIR), target blood glucose (TBG), RI, BG and carbs intake inputted by the user.

The recommended bolus is calculated as:

$$\text{Recommended bolus} = \underbrace{(TC/CIR)}_{\text{"Food estimate"}} + \underbrace{(CBG - TBG)/IS}_{\text{"Correction estimate"}} - RI$$

where TC—total amount of carbohydrates; CIR—carbohydrate-to-insulin ratio; TBG—target blood sugar; CBG—current blood sugar; IS—insulin sensitivity; and RI—residual insulin.

The residual insulin is also considered in the bolus recommendation feature described in co-owned/co-pending U.S. publication no. US2008/0234663 and international patent application no. PCT/IL2009/000454, the disclosures of which are incorporated herein by reference in their entireties. This bolus recommendation feature comprises sets of grids/tables of ranges of carbohydrate and blood glucose level. Each grid corresponds to a different combination of IS, CIR, and TBG. Additional grids correspond to selected bolus doses and residual insulin values. The final recommended dose is related to a value that is substantially equivalent to the selected bolus dose minus the RI.

Application of the abovementioned rule (as shown in FIG. 1) can lead to over- or under-dosing of insulin due to significant individuality variability of insulin absorption and consumption which varies among different patients. The assumption that the complete bolus absorption time (a state in which there is no residual insulin, RI=0) is always 5 hours (i.e. assuming 20%/hour), ignores the individual variability, and, as a result, may not be correct. A more accurate, user specific assessment of the RI time is described in co-owned, co-pending international publication no. WO2009/060433, the disclosure of which is hereby incorporated by reference in its entirety. Generally, the described procedure for assessing residual insulin (RI) time of a patient comprises: allowing the patient to fast during a period of time, determining a known amount of carbohydrates to be administered to the patient, based on the determined amount of carbohydrates, administering an insulin bolus to the patient, administering the determined amount of carbohydrates to the patient, subsequently periodically measuring blood glucose (BG) levels of the patient at predetermined times for indication of at least two successive substantially equal values, or values within a predetermined range, and calculating the RI time based on the time span between the insulin administration to the first measurement of the at least two successive equal values.

Figure 2:
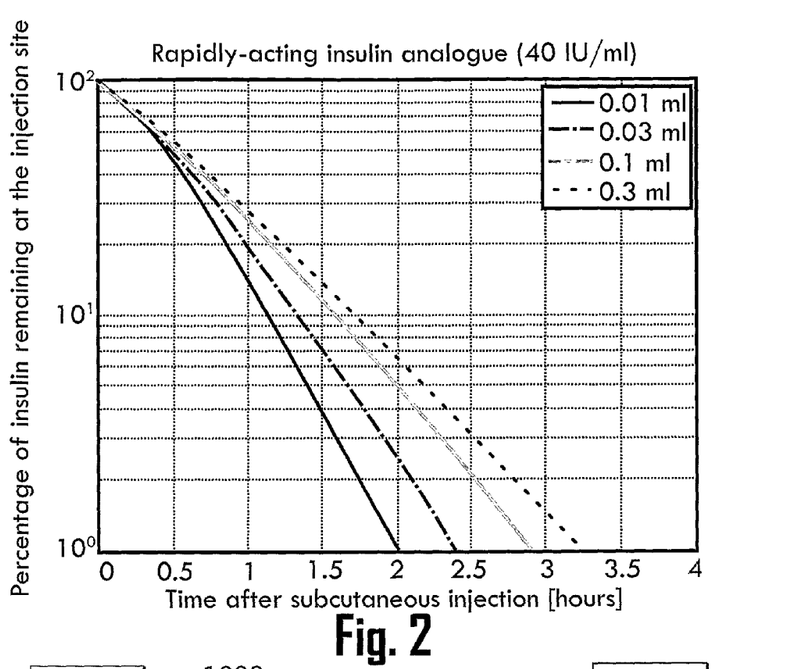
FIG. 2 is a graph of RI vs. time for various bolus doses (dose dependent RI time).

Furthermore, it has been shown that the remaining insulin time is volume dependent. For example, at a certain concentration (e.g., 100 U/ml), a smaller insulin volume (e.g., 2 U) is absorbed faster than a larger volume (e.g., 20 U) (Journal of Diabetes Science and Technology, 2007 Vol. 1 (5), pp. 780-793). FIG. 2 shows an example of a graph of the percentage of insulin remaining at the injection site versus elapsed time after subcutaneous injection. It can be seen that the lower the subcutaneously injected volume, the steeper is the decline of the percentage of insulin remaining at the injection site as a function of time after the injection. In other words, it can be seen that the RI time is a function of the injected dose—the lower the dose, the shorter the RI time.

SUMMARY

The present disclosure describes embodiments directed to devices, systems and methods for infusing insulin. Some embodiments are directed to devices, systems and methods for adjusting RI time according to at least one bolus dose. In some embodiments, an infusion device comprises a memory device that stores respective RI time values for different insulin doses, and a processor-based device configured to correlate the bolus dose with the respective RI time. In some embodiments, the device includes a glucose monitor (e.g., glucometer) which may be a continuous glucose monitor (CGM). In some embodiments, the device includes a remotely controlled skin adherable dispensing unit that may include a reusable part and a disposable part.

In some embodiments, the RI time for various insulin doses (e.g., 2 U, 5 U, and 8 U) can be determined based on consecutive glucose level measurements (continuous or periodic) after a meal, and corresponding insulin injection. The RI time is the time elapsed until a glucose level plateau is reached, as described, for example in co-owned, co-pending international publication No. WO2009/060433, the content of which is hereby incorporated by reference in its entirety. RI time for all doses can be determined (e.g., interpolated, extrapolated, rounded, truncated, set to the nearest multiple of some fraction, etc.) based on tested doses.

For example, the RI time periods for 2 U, 5 U, and 8 U are 3, 3.5, and 5 hours respectively. If the user delivers a bolus dose of 4 U, the RI time can be interpolated to yield 3.3 hours (between 3 hours and 3.5 hours). Alternatively, the RI time can be set to the nearest tested bolus dose, which in this case is 3.5 hours (respective RI time of 5 U). Similarly, if the user delivers a bolus dose of 9 U, the RI time can be extrapolated to 5.1 hours or rounded to 5 hours.

In some embodiments, calculation of a meal bolus dose is typically based on summation of previous RIs based on the dose adjusted RI time. For example, given a meal that requires absolute value of 7 U, occurring 3 hour after an 8 U meal and 1 hour after a 3 U meal, a recommendation of delivering 1.8 U would be effected:

RI from the 8 U meal is 3.2 U, i.e., RI=8 U−8 U*(3/RI time)=8 U−8 U*3/5=3.2 U.

RI from the 3 U meal is 2 U, i.e., RI=3 U−3 U*(1/RI time)=3 U−3 U*1/3=2 U.

Thus, covering the current meal (i.e., the 7 U meal) that requires 7 U would require 1.8 U (i.e., 7 U−(3.2 U+2 U)=1.8 U).

According to some embodiments, the RI time for a plurality of doses can be assessed and a graph of bolus dose versus RI time can be generated.

In some embodiments, a drug delivery system for administration of insulin to a body of a patient is disclosed. The system includes a processor-based device implementing at least a residual insulin (RI) determination unit, the RI determination unit configured to determine a residual insulin in the patient's body at a particular time instance based on one or more bolus doses previously delivered to the body of the patient, each of the one or more bolus doses being associated with at least one dose value and an associated time representative of the time the at least one dose value was delivered to the body of the patient, and based on one or more dose dependent RI time records, each of the one or more dose dependent RI time records includes at least a dose value and an associated at least a duration value representative of dose-dependent duration of therapeutic effectiveness of the associated at least the dose value. The system also includes a pump to controllably dispense the insulin from a reservoir to the body of the patient based on the residual insulin determined by the RI determination unit.

Embodiments of the system may include any of the features described in the present disclosure, including any of the following features.

The duration value of at least one of the one or more dose dependent RI records may be based on one or more of, for example, insulin type, site of cannula insertion and insulin delivery, physical activity, body temperature, fluid absorption characteristics, weight, age, gender, CIR, IS, and/or concentration of insulin.

The RI determination unit may further be configured to determine a bolus amount to be delivered to the patient's body based on determined residual insulin. The pump configured to controllably dispense the insulin may be configured to deliver the determined bolus amount to the patient's body.

The RI determination unit configured to determine the residual insulin based on the one or more bolus records and the one or more dose dependent RI time records may be configured to determine the residual insulin in the patient's body by performing one or more of, for example, matching, using data tables, a dose value of at least one of the one or more bolus records to data corresponding to the one or more of the dose dependent RI time records arranged in the data tables, and/or determining the residual insulin value for the dose value of the at least one of the one or more bolus doses using relationships, determined based on the data corresponding the one or more dose dependent RI time records, that relate the dose value of the at least one of the one or more bolus records to a corresponding RI time determined using the determined relationship.

The RI determination unit configured to determine the residual insulin based on the one or more bolus records and the one or more dose dependent RI time records may be configured to determine for a delivered bolus of at least one of the one or more bolus records an associated RI time equivalent to the duration value associated with a dose value from the one or more dose dependent RI time records closest in value to a dose value of the delivered bolus.

The RI determination unit configured to determine the residual insulin based on the one or more bolus records and the one or more dose dependent RI time records may be configured to generate a graph of RI time versus bolus dose based, at least in part, on the one or more dose dependent RI time records, and determine an RI time for a given delivered bolus value from one of the one or more bolus records in accordance with the generated graph.

The RI determination unit configured to determine the residual insulin based on the one or more bolus records and the one or more dose dependent RI time records may be configured to determine for each of the one or more bolus records an associated individual residual insulin at the particular time instance based, at least in part, on the one or more dose dependent RI time records, and determine a sum of the determined individual residual insulin for each of the one or more bolus records.

The RI determination unit configured to determine the sum of the determined individual residual insulin may be configured to determine a weighted sum of the determined individual residual insulin according to the relationship $$\sum_{j=1}^{n} \alpha_j RI_j,$$

where $RI_j$ is the determined individual residual insulin for the $j^{th}$ bolus record from the one or more bolus records, and $\alpha_j$ is an associated weight to apply to the determined residual insulin.

The RI determination unit configured to determine the residual insulin based on the one or more bolus records and the one or more dose dependent RI time records may be configured to tailor the residual insulin to the patient based on patient-specific characteristics. The RI determination unit configured to tailor the residual insulin may be configured to tailor the residual insulin using at least one of, for example, linear curve fitting, non-linear curve fitting, Bayesian models, neural network, fuzzy logic, genetic algorithms, linear regression, machine learning procedures, and/or statistical learning procedures.

A duration value of one of the one or more dose dependent RI time records for a bolus used to cover a meal with a low glycemic index (GI) or glycemic load (GL) is lower than another duration value of another of the one or more dose dependent RI time records used to cover a meal with high glycemic index.

The RI determination unit may be located in a remote control.

The system may further include a screen to display at least the residual insulin determined by the RI determination unit.

The system may further include a user interface for receiving at least one of, for example, a dose value associated with at least one of the one or more bolus doses previously delivered to the body of the patient, an associated time representative of the time the dose value was delivered to the body of the patient, a dose value of at least one of the one or more dose dependent RI time records, a duration value associated with the dose value of the at least one of the one or more dose dependent RI time records, and/or a confirmation of the user.

The user interface may include at least one of, for example, buttons, switches, keys, a keyboard, a touch-sensitive screen, and/or a voice command interface.

The system may further include a transceiver configured to receive and/or transmit data related to operation of the RI determination unit.

In some embodiments, a method for determining residual insulin (RI) for use with an insulin delivery device is disclosed. The method includes receiving one or more bolus records, each bolus record includes at least one dose value and an associated time representative of the time the at least one dose value was delivered to a patient, and receiving one or more dose dependent RI time records, each of the one or more RI time records includes at least a dose value and an associated at least a duration value representative of dose-dependent duration of therapeutic effectiveness of the associated at least the dose value. The method also includes determining based on the one or more bolus records and the one or more dose dependent RI time records a residual insulin in the patient's body at a particular time instance.

Embodiments of the method include any of the features described in the present disclosure, including any of the features described above in relation to the system and any of the following features.

The method may further include determining a bolus amount to be delivered to the patient's body based on determined residual insulin. The method may further include delivering the determined bolus amount to the patient's body.

Determining based on the one or more bolus records and the one or more dose dependent RI time records the residual insulin in the patient's body at the particular time instance may include determining the residual insulin in the patient's body by performing one or more of, for example, matching, using data tables, a dose value of at least one of the one or more bolus records to data corresponding to the one or more of the dose dependent RI time records arranged in the data tables, and/or determining the residual insulin value for the dose value of the at least one of the one or more bolus doses using relationships, determined based on the data corresponding the one or more dose dependent RI time records, that relate the dose value of the at least one of the one or more bolus records to a corresponding RI time determined using the determined relationship.

Determining based on the one or more bolus records and the one or more dose dependent RI time records the residual insulin in the patient's body at the particular time instance may include determining for a delivered bolus of at least one of the one or more bolus records an associated RI time equivalent to the duration value associated with a dose value from the one or more dose dependent RI time records closest in value to a dose value of the delivered bolus.

Determining based on the one or more bolus records and the one or more dose dependent RI time records the residual insulin in the patient's body at the particular time instance may include generating a graph of RI time versus bolus dose based, at least in part, on the one or more dose dependent RI time records, and determining an RI time for a given delivered bolus value from one of the one or more bolus records in accordance with the generated graph.

Determining based on the one or more bolus records and the one or more dose dependent RI time records the residual insulin in the patient's body at the particular time instance may include determining for each of the one or more bolus records an associated individual residual insulin at the particular time instance based, at least in part, on the one or more dose dependent RI time records, and determining a sum of the determined individual residual insulin for each of the one or more bolus records.

Determining the sum of the determined individual residual insulin may include determining a weighted sum of the determined individual residual insulin according to the relationship $$\sum_{j=1}^{n} \alpha_j RI_j,$$

where $RI_j$ is the determined individual residual insulin for the $j^{th}$ bolus record from the one or more bolus records, and $\alpha_j$ is an associated weight to apply to the determined residual insulin.

Determining based on the one or more bolus records and the one or more dose dependent RI time records the residual insulin in the patient's body at the particular time instance may include tailoring the residual insulin to the patient based on patient-specific characteristics.

Tailoring the residual insulin may be performed using at least one of, for example, linear curve fitting, non-linear curve fitting, Bayesian models, neural network, fuzzy logic, genetic algorithms, linear regression, machine learning procedures, and/or statistical learning procedures.

In some embodiments, a computer program product comprising computer instructions stored on a non-transitory computer readable storage device is disclosed. The computer instructions, when executed on one or more processor-based devices, cause the one or more processor-based devices to receive one or more bolus records, each bolus record includes at least one dose value and an associated time representative of the time the at least one dose value was delivered to a patient, and to receive one or more dose dependent RI time records, each of the one or more RI time records includes at least a dose value and an associated at least a duration value representative of dose-dependent duration of therapeutic effectiveness of the associated at least the dose value. The computer instructions also cause the one or more processor-based devices to determine based on the one or more bolus records and the one or more dose dependent RI time records a residual insulin in the patient's body at a particular time instance.

Embodiments of the computer program product may include any of the features described in the present disclosure, including the above-described features of the system and method.

In some embodiments, a system to determine residual insulin (RI) for use with an insulin delivery device is disclosed. The system includes means for receiving one or more bolus records, each bolus record includes at least one dose value and an associated time representative of the time the at least one dose value was delivered to a patient, and means for receiving one or more dose dependent RI time records, each of the one or more RI time records includes at least a dose value and an associated at least a duration value representative of dose-dependent duration of therapeutic effectiveness of the associated at least the dose value. The system also includes means for determining based on the one or more bolus records and the one or more dose dependent RI time records a residual insulin in the patient's body at a particular time instance.

Embodiments of the computer program product may include any of the features described in the present disclosure, including the above-described features of the system, the method, and the computer program product.

Details of one or more implementations are set forth in the accompanying drawings and in the description below. Further features, aspects, and advantages will become apparent from the description, the drawings, and the claims.

DETAILED DESCRIPTION

FIG. 1 is a chart of residual insulin at different hours (1-5) after insulin Lispro bolus administration. It can be seen that, based on this chart, a constant percentage (20%) of the given bolus is consumed every hour regardless of the bolus dose (i.e., volume). That is, all doses have a RI time of 5 hours. Therefore, with this methodology of residual insulin calculation, the residual insulin calculation is dose-independent.

FIG. 2 is a graph of the percentage of insulin remaining (at an injection site) versus time after subcutaneous injection (graph adapted from the Journal of Diabetes Science and Technology, 2007 Vol. 1 (5), 780-793). It can be seen, for example, that 0.4 U of insulin is substantially entirely depleted within 2 hours while 4 U is substantially entirely depleted within 2.8 hours. In other words, the smaller the subcutaneously injected volume, the steeper the decline in the percentage of insulin remaining at the injection site as a function of time. Thus, here the residual insulin is shown to be dose-dependent.

Figure 3A:
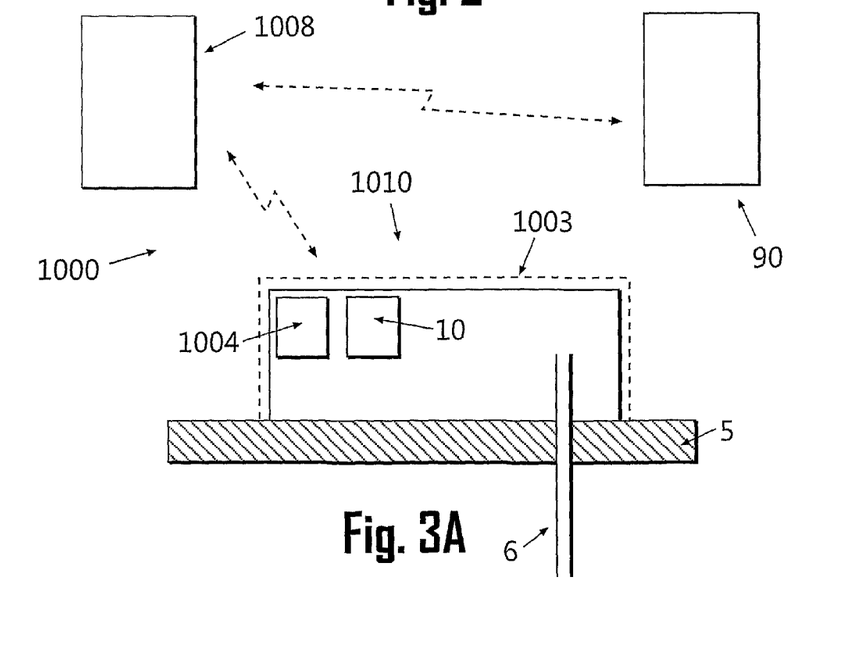
FIGS. 3a-c are schematic diagrams of an example fluid delivery device that includes an insulin dispensing unit and a remote control unit, and which may include a dose dependent RI time feature.
Figure 3B:
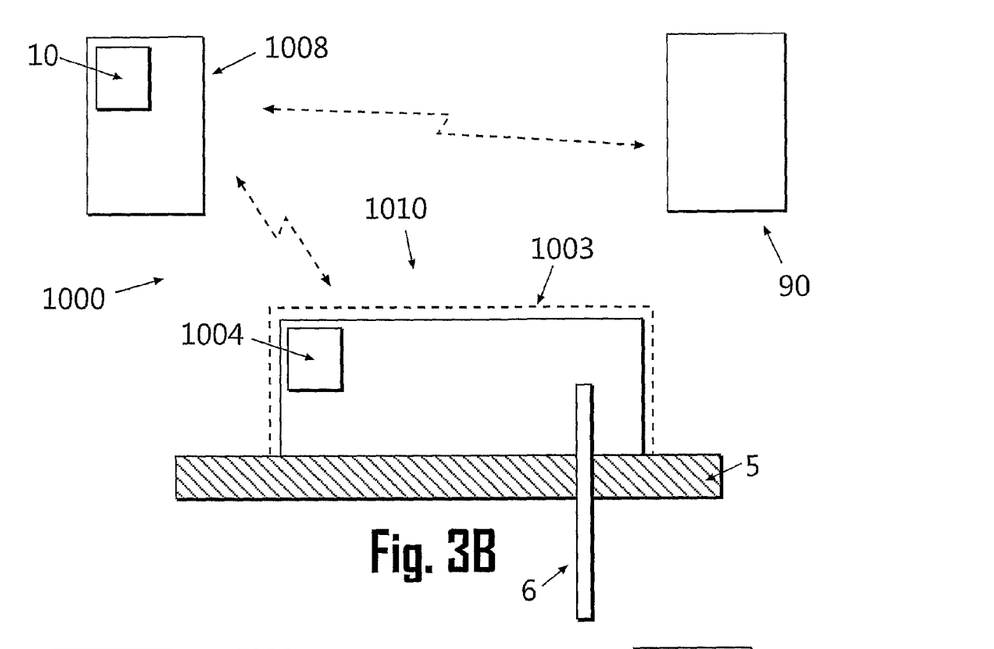
Figure 3C:
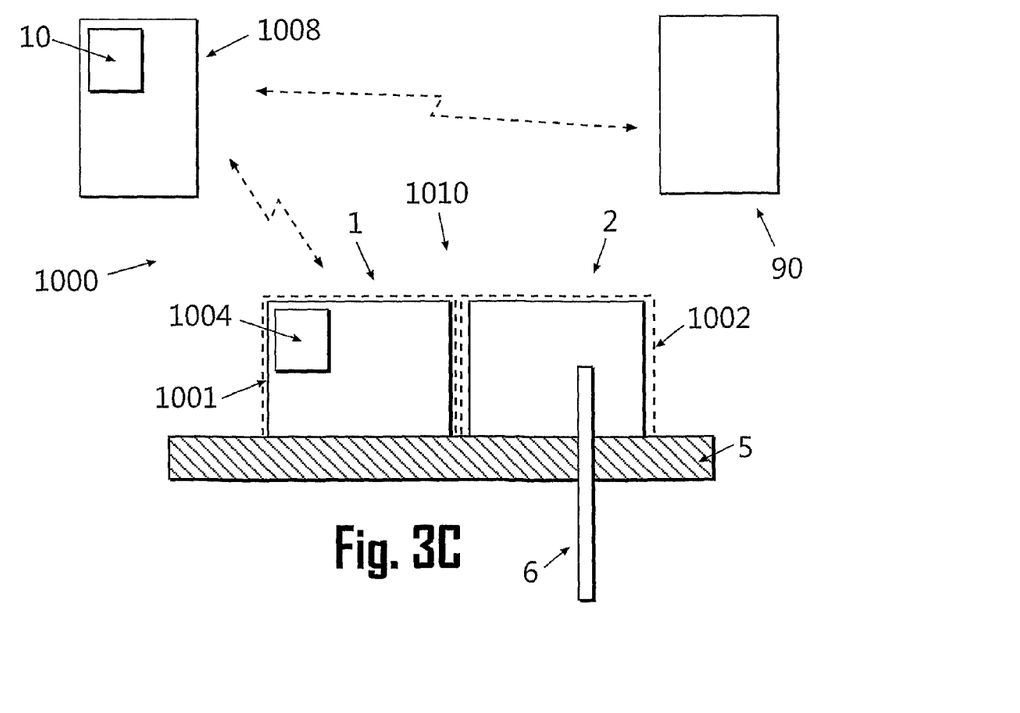

FIGS. 3a-c illustrate embodiments of a system 1000 according to some embodiments. The system 1000 can be used for dispensing therapeutic fluids (e.g., insulin) to the body of the patient. In some implementations, the system includes a dispensing unit 1010, a remote control unit 1008, and a blood glucose (BG) monitor 90. In some embodiments, the dispensing unit is connected to a cannula 6 that penetrates a patient's skin 5 to deliver insulin to the subcutaneous tissue. The dispensing unit may include a single part having a single housing 1003, as shown in FIGS. 3a-b, or may include two parts having two separate connectable housings 1001, 1002. In some embodiments, a first part can be a reusable part 1 and a second part can be disposable (disposable part 2), as shown in FIG. 3c. Flow programming and data acquisition can be done by the remote control unit 1008 or directly by one or more operating buttons/switches 1004 located on the dispensing unit housing. A BG monitor or a continuous glucose monitor (CGM) may be located at the remote control unit and/or the dispensing unit. In some embodiments, the remote control unit may be implemented in one of a Personal Data Assistance (PDA), a cellular phone, a watch, an iPod (i.e., a media player), an iPhone, a laptop, a PC, some other processor-based device, etc.

In some embodiments, an RI feature 10 for dose dependent RI time adjustment and RI determination/calculation may be located in the dispensing unit 1010 (see FIG. 3a), in the remote control unit 1008 (as shown in FIGS. 3b-c) and/or implemented using the two units 1010 and 1008. Such a dispensing unit and/or remote control device/system is disclosed in co-owned co-pending U.S. publication no. US2007/0106218 and in co-owned, co-pending international application no. PCT/IL09/000,388, the contents of which are herein incorporated by reference in their entireties.

In some embodiments, the remote control unit 1008 and/or dispensing unit 1010 containing the RI feature 10 (also referred-to as RI calculator, RI module, and/or RI determination unit) for dose-dependent RI time adjustment and RI determination may include a memory device, a user interface such as a keypad and/or any other input mechanisms (e.g., buttons, switches, keys, touch-screen, voice command interface, etc.), a display/screen and/or other notification (or output) devices such as audible output device (e.g., buzzer) and/or vibration output devices (e.g., a vibrator) to notify/alert the user. The keypad and/or input devices can be used for programming and commanding the dispensing patch unit 1010 and/or the RI feature 10 for dose dependent RI time adjustment and RI calculation. In some embodiments, the dispensing unit (which may include a pump) may controllably dispense insulin based, at least in part, on the determined residual insulin. In some embodiments, the remote control unit 1008 and/or dispensing unit 1010 may also include a transceiver to enable transmission and receipt (wirelessly and/or through wired-connections) of data and/or commands relating to the operation of the RI feature (RI determination unit). In some embodiments, the user interface is configured to receive at least one of, for example, a dose value associated with at least one of the one or more bolus doses previously delivered to the body of the patient, an associated time representative of the time the dose value was delivered to the body of the patient, a dose value of at least one of the one or more dose dependent RI time records, an associated duration value of the at least one of the one or more dose dependent RI time records, and a confirmation of the user regarding the data (e.g., confirmation of the accuracy of the bolus doses).

According to some embodiments, continuous glucose readings may be transmitted to the remote control and/or patch unit from a stand-alone sensing apparatus (e.g., CGM). Alternatively and/or additionally, a sensing apparatus can be contained or integrated within the patch unit. This sensing apparatus may be included in the reusable part, may be included in the disposable part, or may be shared between the reusable part and the disposable part. The dispensing apparatus (i.e., the mechanism responsible of dispensing the fluid to the user's body) may be coupled to a cannula and the sensing apparatus may be coupled to a separate probe/sensor. In some embodiments, both apparatus (dispensing and sensing) may be connected to a single cannula/probe as described in greater detail in, for example, co-owned/co-pending US publication US2007/0191702 and in international publications nos. WO2008/078319 and WO2009/066288, the disclosures of which are incorporated herein by reference in their entireties. In some embodiments, the sensing apparatus can include a separate unit and/or incorporated within the dispensing unit, and the RI feature for dose dependent RI time adjustment and RI determination can be included in the remote control unit.

In some embodiments, the therapeutic fluid (e.g., insulin) can be dispensed based on analyte (e.g., glucose) sensing (e.g., CGM readings) using a closed loop mode/system implementation or in a semi-closed loop mode/system, according to analyte readings (comprising analyte concentration) and/or based on additional inputs (e.g., pre-meal bolus). For example, the dose dependent RI determination in a semi-closed loop system can be used for bolus calculation.

Figure 4:
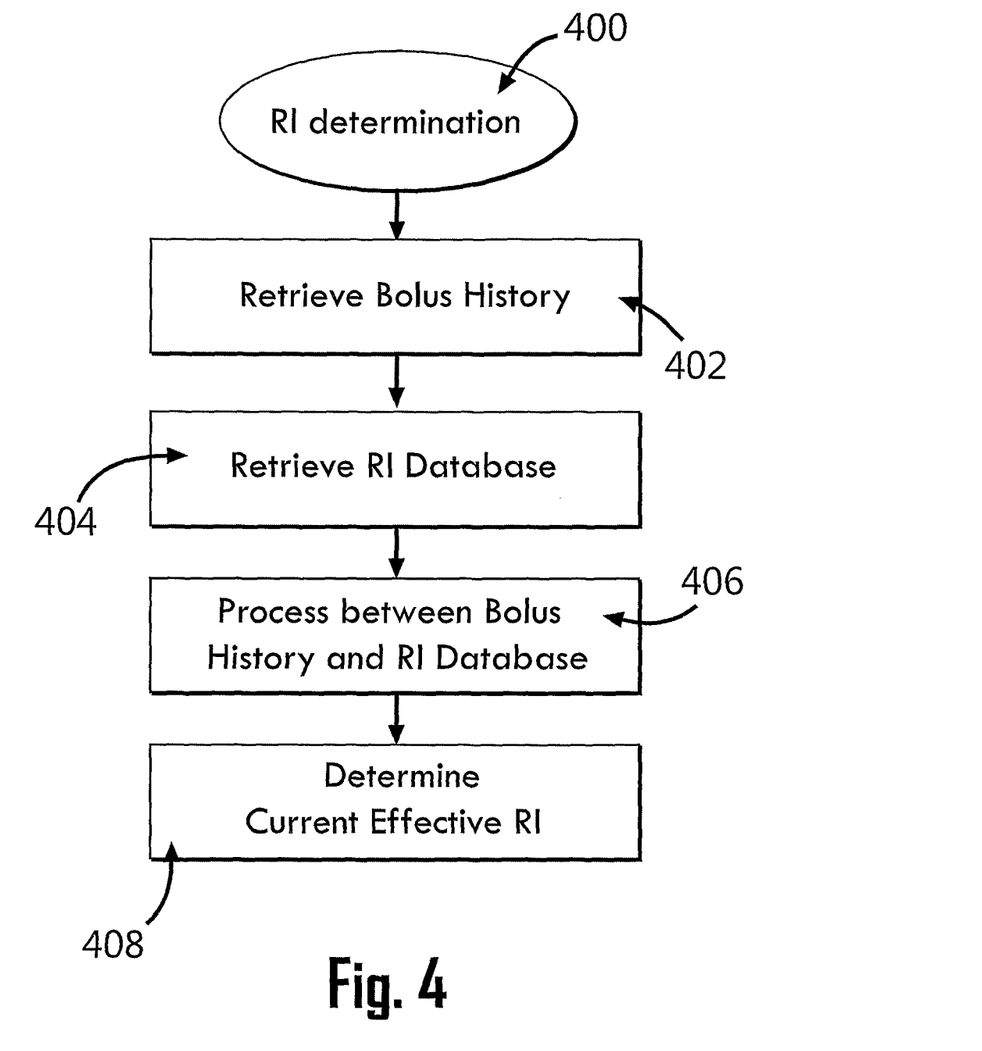
FIG. 4 is a flowchart of an example procedure for RI determination.

FIG. 4 is a flowchart of an example procedure for RI determination, implementing the bolus dependent RI time, according to some embodiments of the present disclosure. Briefly, in performing the procedure, at least one of the operations depicted in FIG. 4 may be performed. In some embodiments, a plurality of the depicted operations of FIG. 4 may be performed, and in some embodiments, all of the depicted operations may be performed. As shown, an RI value (also referred-to as "Current Effective RI") may be determined 400 based on a relationship (e.g., mathematical, empirical, approximation, etc.) between one or more boluses and an RI time. A Bolus History may then be retrieved 402, and an RI Database may also be retrieved 404. Then, by correlating 406 the data of the Bolus History and the RI Database, a Current Effective RI can be determined (e.g., calculated). In some embodiments, correlating the data of bolus history and the RI database includes determining from dose-dependent data obtained from the RI database an estimate or approximation of the RIs for the administered bolus schedule (obtained from the bolus history) at a particular time. These determined approximations of the effective RI in a body of a patient at a particular time thus enable determining the bolus dosage required for a particular meal that is to be consumed by the patient at that particular time.

In some embodiments, the RI time Database can be a database stored in one or more memory storage devices (which may be distributed across a network connecting the memory storage devices) which store doses and corresponding RI times. In some embodiments, the RI Database can include formulations, scripts, expressions, functions, operators (e.g., analytic, numeric, empiric) that can be used to determine correlations between a bolus dose and an RI time. The dose dependent RI time can be further associated or dependent (e.g., be a function of) on one or more of the following parameters: insulin type (e.g., rapid acting insulin, regular insulin), site of cannula insertion and insulin delivery, physical activity, body temperature, fluid absorption characteristics, weight, age, gender, CIR, IS, concentration of insulin and other known health related parameters of the user. According to some embodiments, the RI Database can be created/generated via a window/screen of the user interface of the device where the user or caregiver can enter/input at least one dose dependent RI time, by implementing an RI time determination test as described, for example, in co-owned, co-pending international publication no. WO2009/060433, the disclosure of which is incorporated herein by reference in its entirety, or by performing other suitable RI database generation procedures. In some embodiments, the RI time Database can include one or more tables (e.g., schedules, look-up tables) receivable or downloadable from a remote source (e.g., from the web or a PC, wirelessly or through an appropriate connector).

As noted, in performing the procedure of FIG. 4, the bolus history may be retrieved 402. The Bolus History, in some embodiments, includes one or more records specifying an amount of therapeutic fluid ("dose") and time of its administration ("t"). In some embodiments, the bolus history may further include the type of bolus, e.g., "normal bolus" where the entire bolus dose is delivered at the highest delivery rate enabled by the delivery device (e.g., pump), "extended bolus" where the entire bolus dose is delivered over a relatively long period of time at a constant rate, "combined bolus" where a portion of the bolus dose is delivered as an immediate bolus at a first rate and another portion (e.g., the rest of the bolus dose) delivered as an extended bolus employing a second rate, etc. The Bolus History can be stored in a memory storage device located in the delivery device and/or on one or more external devices (e.g., cellular phone, PC, web-based application, and the like).

After retrieving data from the Bolus History and from the RI Database, the data from the Bolus History may be processed (e.g., correlated, matched, etc.) 406 with the data of RI Database (also referred-to as "RI time Database") to determine the corresponding RI value for each bolus dose. The processing can be done via matching tables or matrices, performing computation/correlation procedures (which may be represented, at least partly, as mathematical formulations), etc. In some embodiments, the mathematical formulations representative of the correlation techniques/behavior employed can be obtained by implementing curve fitting of data specific for the patient (i.e., tailored), by implementing other types of optimization and/or regression procedures, etc.

As further shown in FIG. 4, a majority, or substantially all, or in some embodiments, all the bolus dependent RI values, may be taken into account to determine the Current Effective RI. According to some embodiments, the Current Effective RI can include a simple summation of all RI's (e.g., $RI_1 + RI_2 \ldots + RI_n$). Alternatively, the Current Effective RI can include a weighted summation (e.g., $$\left(e.g., \sum_{j=1}^{n} \alpha_i RI_j\right),$$

i.e., a particular RI may have more or less influence. For example, the RI from a bolus used to cover a meal with a low glycemic index (GI) or glycemic load (GL) may have less influence on the Current Effective RI than the RI from a bolus used to cover a meal with high glycemic index. The GI can be expressed as a ranking/indexed schedule for carbohydrates contained in food according to how they affect the blood glucose levels. For example, in some embodiments, the fastest-acting carbohydrate, glucose, is given a value of 100, and the other carbs are ranked relative to that value. A low GI food will release glucose more slowly and steadily than food containing high GI (high GI food causes a more rapid rise in blood glucose).

In some embodiments, procedure of FIG. 4 can further include the generation of a dose-dependent RI time Database associated with different values of bolus doses and/or the generation of the Bolus History.

Figure 5:
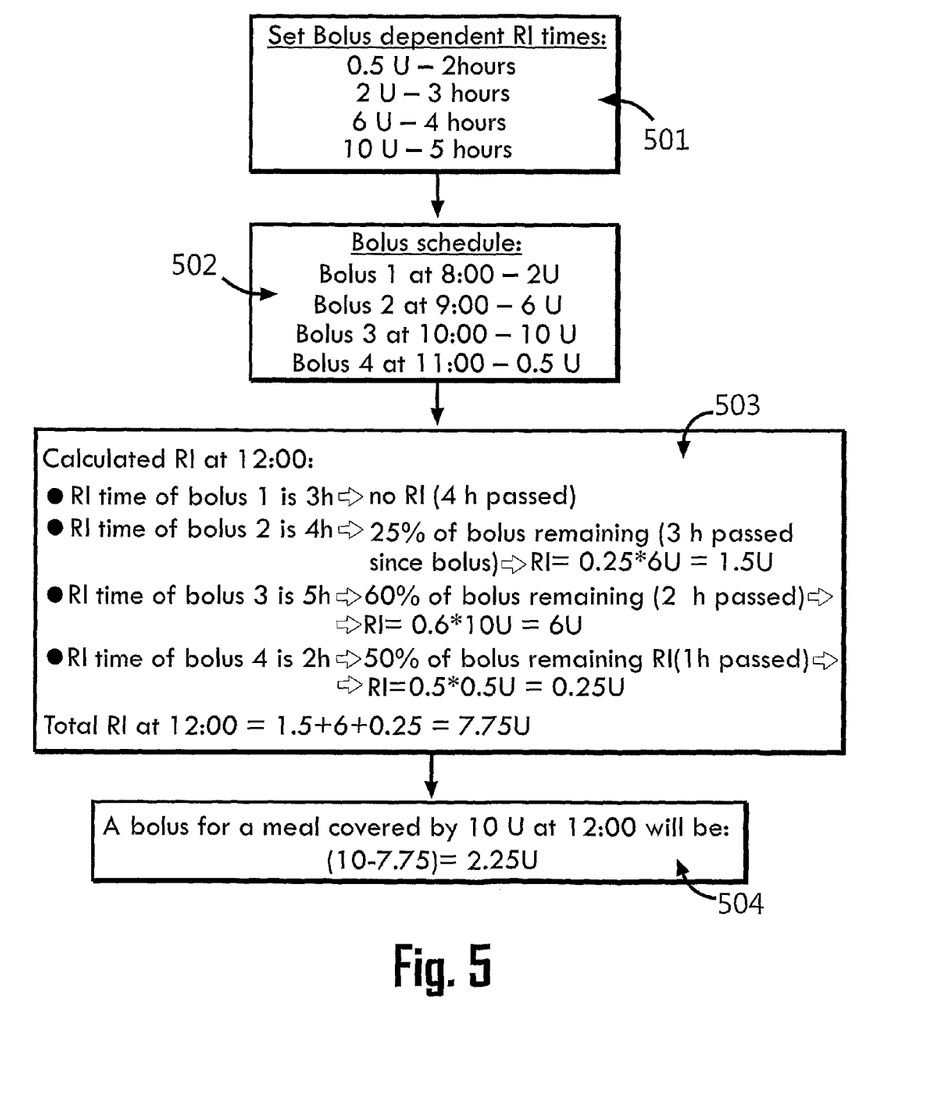
FIG. 5 is a flowchart of an example procedure for bolus determination implementing a bolus dependent RI time feature.

FIG. 5 is a flow chart of an example procedure for bolus determination according to the bolus dependent RI time. As shown, dose dependent RI times are presented (e.g., retrieved, determined, or otherwise obtained) 501. For example, the RI times of 0.5, 2, 6, and 10 insulin units, are 2, 3, 4, and 5 hours, respectively. As noted above, The RI times can be determined for example by the method described in, for example, co-owned, co-pending international publication no. WO2009/060433. Additionally, an exemplary bolus schedule may be obtained 502. In the example illustrated in FIG. 5, Boluses comprising 2, 6, 10, and 0.5 units have been delivered at 8:00, 9:00, 10:00, and 11:00 o'clock respectively. If a linear consumption of the bolus is assumed (i.e., the graph of residual insulin versus DIA is linear), the RI determined (e.g., computed/calculated) 503 at 12:00 o'clock is 7.75 units, which is the sum of 0 units of insulin contributed by bolus 1 (because its RI time has elapsed), 1.5 units of insulin contributed by bolus 2, 6 units of remaining effective insulin contributed by bolus 3, and 0.25 units of remaining effective insulin contributed by bolus 4. In some embodiments, other behavioral profiles (or regimens), such as exponential or polynomial behaviors, may be used to determine the RI.

With continued reference to FIG. 5, in the illustrated example, a meal covered by 10 units is to be consumed at 12:00 o'clock. Since the calculated RI at 12:00 is 7.75, the recommended bolus dose is determined 504 to be 2.25 U (10-7.75).

By contrast, the calculated RI when using dose independent RI time determination (computation) methodology (as shown for example in FIG. 1) may be (according to some embodiments):

Assumption: RI time=20%/hour=5 hours
RI of bolus 1=2 U*20%=0.4 U (4 h passed from a 2 U bolus)
RI of bolus 2=6 U*40%=2.4 U (3 h passed from a 6 U bolus)
RI of bolus 3=10 U*60%=6 U (2 h passed from a 10 U bolus)
RI of bolus 4=0.5*80%=0.4 U (1 h passed from a 0.5 U bolus)
Total RI at 12:00=0.4 U+2.4 U+6 U+0.4 U=9.2 U Thus, using the dose-independent determination methodology, for a meal consumed at 12:00 pm (for example) that should be covered by 10 units, the recommended bolus dose would be determined as 10 U−9.2 U=0.8 U.

Figure 6:
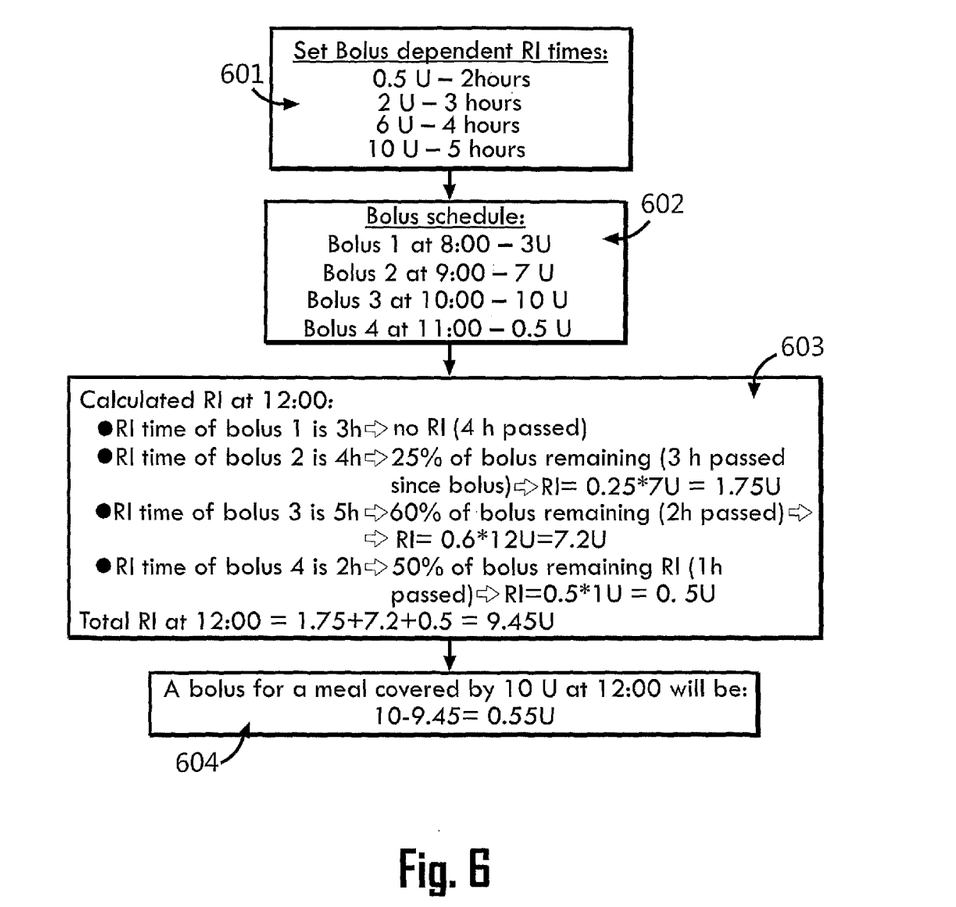
FIG. 6 is a flowchart of a further example procedure for bolus determination implementing a bolus dependent RI time feature.

FIG. 6 depicts a block diagram of another example procedure for bolus determination according to the bolus dependent RI time according to some embodiments of the disclosure. As shown, dose dependent RI times of tested boluses are obtained 601. For example, the RI time of 0.5, 2, 6, and 10 insulin units are 2, 3, 4, and 5 hours, respectively. Additionally, an example bolus schedule is obtained (presented) 602. The boluses in the schedule include boluses of 3, 7, 12, and 1 units, delivered, in the example depicted in FIG. 6, at 8:00, 9:00, 10:00, and 11:00 am, respectively. In the given example, the RI time of the exact boluses delivered have not been tested. According to some embodiments, the RI time of the delivered bolus may thus be determined by selecting the RI time of the nearest tested bolus dose (as noted herein, RI times for bolus schedule may be determined based on other techniques/procedures that use the RI data of the test boluses, including such techniques/procedures as extrapolation, interpolation, curve fitting, linear regression, etc.) In the given example, the RI time of bolus 1, which includes 3 units, is determined to be 3 hours because the closest available tested bolus RI (obtained at 601) is for a bolus dose of 2 units. In the same manner, the RI time of bolus 2, which comprises 7 U would be 4 hours (since the A dose is 6 U). So, based on an assumed linear consumption of the bolus (in this particular example), the RI determined 603 at 12:00 o'clock for the given bolus schedule, is 9.45 units, determined as 0 units of insulin contributed by bolus 1 (since the RI time has passed), 1.75 units of insulin contributed by bolus 2, 7.2 units of insulin contributed by bolus 3, and 0.5 units of insulin contributed by bolus 4. As further illustrated in the example of FIG. 6, a meal covered by 10 units is to be consumed at 12:00 o'clock. Because the determined RI at 12:00 is 9.45 U, the recommended bolus dose is determined 604 to be 0.55 U (10 U−9.45 U).

Figure 7:
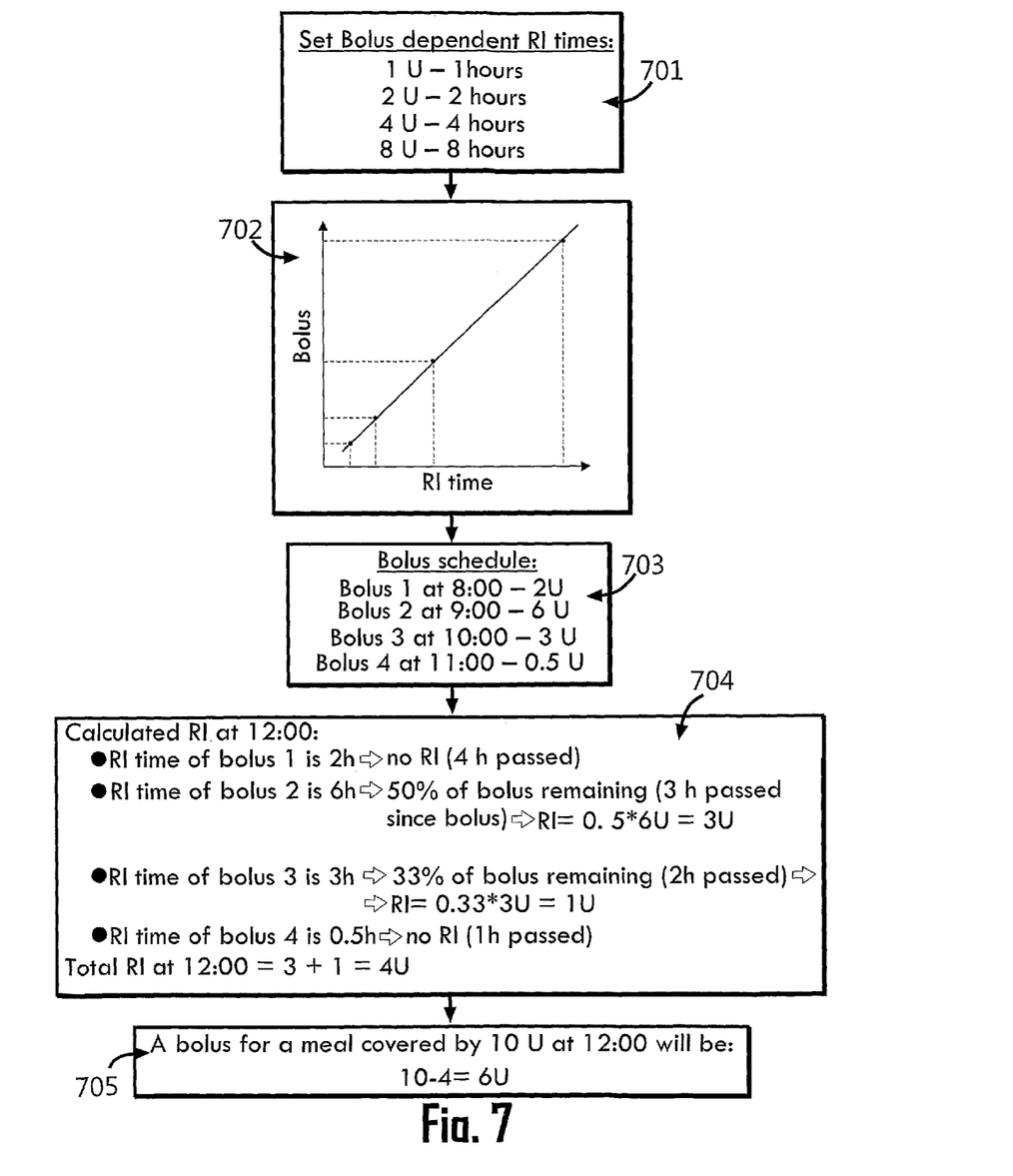
FIG. 7 is a flowchart of another example method for bolus determination implementing a bolus dependent RI time feature.

FIG. 7 is a block diagram of another depicted example procedure for bolus determination based on bolus dependent RI time, according to some embodiments of the present disclosure. As shown, dose dependent RI times of tested boluses are obtained 701. For example, the RI times of 1, 2, 4, and 8 insulin units, are 1, 2, 4, and 8 hours, respectively. A relationship representing the RI time versus bolus dose is determined or otherwise obtained 702. In this example, such a relationship is represented by a generated graph plotting the RI time versus the bolus dose. As shown in the graph, a linear curve is plotted. Yet, in some embodiments, other behaviors (e.g., exponential) may be used. As further shown in FIG. 7, a bolus schedule is obtained (e.g., retrieved and/or presented) 703. In this example, the boluses in the schedule include boluses of 2, 6, 3, and 0.5 units, delivered, in the example of FIG. 7, at 8:00, 9:00, 10:00, and 11:00 o'clock, respectively. In some embodiments, the RI times of the delivered boluses can be determined by obtaining from the RI time versus bolus dose graph (determined or generated at 702) the RI times for the delivered doses. In the given example, because a linear curve has been assumed and computed, the RI time of bolus 1, which includes 2 units, is determined to be 2 hours, the RI time of bolus 2, which includes 6 units, is determined to be 6 hours, the RI time of bolus 3, which comprises 3 U, is determined to be 3 hours, and the RI time of bolus 4, which comprises 0.5 U, is determined to be 0.5 hours. Thus, if a linear consumption of the bolus is assumed, the RI determined 704 at 12:00 o'clock for the given bolus schedule, is 4 units, determined as 0 units of insulin contributed by bolus 1 (since the RI time has elapsed), 3 units of insulin contributed by bolus 2, 1 units of insulin contributed by bolus 3, and 0 units of insulin contributed by bolus 4. As further illustrated in the example of FIG. 7, a meal covered by 10 units is to be consumed at 12:00. Because the determined RI in this example at 12:00 is 4 units, the recommended bolus dose will be 6 U (10–4).

In some embodiments, the above-mentioned RI determination unit (e.g., an RI calculator) and procedures can be implemented to tailor the RI to a specific user based, for example, on user-specific characteristics (e.g., age, weight, overall health, etc.) Deriving the user-specific behavior can be implemented in a self-learning system employing conventional procedures/techniques that include linear or non-linear curve fitting, Bayesian models, neural network, fuzzy logic, genetic algorithms, and the like. Adjusting the RI calculator parameters (or the parameters of the implemented RI determination unit) enables an improved RI determination for each user, thus resulting in improved diabetic care.

Assessing an RI time can be implemented according to implementations described in co-owned, co-pending international publication no. WO2009/060433. The determined RI times can subsequently be used to accurately determine the dose dependent RI's.

Various embodiments of the subject matter described herein can be realized in digital electronic circuitry, integrated circuitry, specially designed ASICs (application specific integrated circuits), computer hardware, firmware, software, and/or combinations thereof. These various embodiments may include implementations in one or more computer programs, stored on non-transitory media, that are executable and/or interpretable on a processor-based systems including, for example, at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a non-transitory machine-readable storage medium that receives machine instructions as a machine-readable signal. The term "machine-readable signal" refers to any signal used to provide machine instructions and/or data to a programmable processor.

To provide for interaction with a user, the subject matter described herein can be implemented on a computer having a display device, e.g., a CRT (cathode ray tube) or LCD (liquid crystal display) monitor, or some other display device, for displaying information to the user, and a keyboard and a pointing device, e.g., a mouse or a trackball, by which the user may provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The subject matter described herein can be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Some embodiments of the present disclosure preferably implement the RI determination unit (e.g., RI calculator) via software operated on a processor contained in a remote control device of an insulin dispensing system and/or a processor contained in a insulin dispensing device being part of an insulin dispensing system.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flow depicted in the accompanying figures and described herein does not require the particular order shown, or sequential order, to achieve desirable results. Other embodiments can be within the scope of the following claims.

What is claimed is:

1. A drug delivery system for administration of insulin to a body of a patient, the system comprising:
   a processor-based device implementing at least a residual insulin (RI) determination unit, the RI determination unit configured to:

receive one or more bolus records, each of the bolus records being associated with a respective bolus dose delivered to the patient and includes at least an associated bolus dose value, an associated time representative of the time the respective bolus dose was delivered to the patient, and an associated duration value representative of dose-dependent duration of therapeutic effectiveness of the associated dose value; and determine a residual insulin in the patient's body based on the associated bolus dose value, the associated time, and the associated duration value associated with each of the one or more bolus records; and a pump to controllably dispense the insulin from a reservoir to the body of the patient based on the residual insulin determined by the RI determination unit.

2. The system of claim 1, wherein the RI determination unit is located in a remote control.

3. The system of claim 1 further including a screen to display at least the residual insulin determined by the RI determination unit.

4. The system of claim 1, further including a user interface for receiving one or more values associated with the one or more bolus records and/or a confirmation of the user.

5. The system of claim 4, wherein the user interface includes at least one of: buttons, switches, keys, a keyboard, a touch-sensitive screen, and a voice command interface.

6. The system of claim 4, further including a transceiver configured to receive and/or transmit data related to operation of the RI determination unit.

7. A method for determining residual insulin (RI) for use with an insulin delivery device, the method comprising:

receiving one or more bolus records, each of the bolus records being associated with a respective bolus dose delivered to a patient and includes at least an associated bolus dose value, an associated time representative of the time the respective bolus dose was delivered to the patient, and an associated duration value representative of dose-dependent duration of therapeutic effectiveness of the associated dose value; and determining, based on the associated bolus dose value, the associated time, and the associated duration value associated with each of the one or more bolus records, a residual insulin in the patient's body at a particular time instance.

8. The method of claim 7, wherein the associated duration value of dose dependent RI records is based on one or more of: insulin type, site of cannula insertion and insulin delivery, physical activity, body temperature, fluid absorption characteristics, weight, age, gender, CIR, IS, and concentration of insulin.

9. The method of claim 7, further comprising: determining a bolus amount to be delivered to the patient's body based on the determined residual insulin.

10. The method of claim 9, further comprising: delivering the determined bolus amount to the patient's body.

11. The method of claim 7, wherein the step of determining the residual insulin in the patient's body at the particular time instance comprises: determining the residual insulin in the patient's body by performing one or more of: matching, using data tables, a first dose value of at least one of the one or more bolus records to data corresponding to one or more dose dependent RI time records arranged in the data tables, and determining the residual insulin value for the dose value of the at least one of the one or more bolus doses using relationships, determined based on the data corresponding the one or more dose dependent RI time records, that relate the dose value of the at least one of the one or more bolus records to a corresponding RI time determined using the determined relationship.

12. The method of claim 7, wherein the step of determining the residual insulin in the patient's body at the particular time instance comprises: determining for a delivered bolus of at least one of the one or more bolus records an associated RI time equivalent to the duration value associated with a dose value from one or more dose dependent RI time records closest in value to a dose value of the delivered bolus.

13. The method of claim 7, wherein the step of determining the residual insulin in the patient's body at the particular time instance comprises: generating a graph of RI time versus bolus dose based, at least in part, on one or more dose dependent RI time records; and determining an RI time for a given delivered bolus value from one of the one or more bolus records in accordance with the generated graph.

14. The method of claim 7, wherein the step of determining the residual insulin in the patient's body at the particular time instance comprises: determining for each of the one or more bolus records an associated individual residual insulin at the particular time instance based, at least in part, on one or more dose dependent RI time records; and determining a sum of the determined individual residual insulin for each of the one or more bolus records.

15. The method of claim 14, wherein determining the sum of the determined individual residual insulin comprises: determining a weighted sum of the determined individual residual insulin according to the relationship $\Sigma_{j=1}^{n} \alpha_j RI_j$ where $RI_j$ is the determined individual residual insulin for the $j^{th}$ bolus record from the one or more bolus records, and $\alpha_j$ is an associated weight to apply to the determined residual insulin.

16. The method of claim 7, wherein the step of determining the residual insulin in the patient's body at the particular time instance comprises: tailoring the residual insulin to the patient based on patient-specific characteristics.

17. The method of claim 16, wherein the step of tailoring the residual insulin is performed by using at least one of: linear curve fitting, non-linear curve fitting, Bayesian models, neural network, fuzzy logic, genetic algorithms, linear regression, machine learning procedures, and statistical learning procedures.

18. The method of claim 7, wherein a duration value of one of the one or more dose dependent RI time records for a bolus used to cover a meal with a low glycemic index (GI) or glycemic load (GL) is lower than another duration value of another of the one or more dose dependent RI time records used to cover a meal with high glycemic index.

19. A computer program comprising computer-executable instructions, which when executed on a suitable computer device, perform the method of claim 7.

20. A non-transitory computer readable medium comprising computer-executable instructions recorded thereon for performing the method of claim 7.

* * * * *